United States Patent [19]
Peters et al.

[11] Patent Number: 5,929,214
[45] Date of Patent: Jul. 27, 1999

[54] THERMALLY RESPONSIVE POLYMER MONOLITHS

[75] Inventors: Eric C. Peters, Hayward; Frantisek Svec, Richmond; Jean M.J. Frechet, Oakland, all of Calif.

[73] Assignee: Cornell Research Foundation, Inc., Ithaca, N.Y.

[21] Appl. No.: 09/030,754

[22] Filed: Feb. 25, 1998

Related U.S. Application Data

[60] Provisional application No. 60/039,221, Feb. 28, 1997.
[51] Int. Cl.$^6$ ............... A23J 1/00; C07K 1/00; C07K 14/00
[52] U.S. Cl. ............................ 530/417; 530/412
[58] Field of Search ................... 530/412, 417; 521/918

[56] References Cited

PUBLICATIONS

*Chemical abstracts,* 127:136433, Peters et al.

*Primary Examiner*—Avis M. Davenport
*Attorney, Agent, or Firm*—Bruce Jacobs

[57] ABSTRACT

Porous polymer monoliths are made thermally responsive by functionalizing/grafting the pores with thermally responsive polymers and copolymers. Depending on the reaction conditions employed, the grafted polymer can either completely block flow through micrometer-sized pores in the monoliths or control the flow rate through the monoliths. The grafted monoliths are useful as thermal gates, thermal valves, and for isocratic hydrophobic interaction chromatography of proteins.

19 Claims, 3 Drawing Sheets

THERMALLY RESPONSIVE POLYMER MONOLITHS

This application claims benefit of Provisional Appl. No. 60/039,221 filed Feb. 28, 1997.

GOVERNMENT RIGHTS

The United States government has certain rights in this invention based upon a grant from the office of Naval Research and the National Institutes of Health (GM-44885).

BACKGROUND OF THE INVENTION

The present invention is directed to thermally responsive synthetic polymer monoliths. More particularly, the present invention is directed to porous synthetic polymer monoliths wherein the pores contain grafted temperature-responsive polymers and copolymers. Depending on the grafting compositions employed, thermally-responsive monoliths can be produced in which the flow through the micrometer sized pores can be controlled (thermal valves) or completely blocked (thermal gates). When the thermally responsive polymers are in their compact form at elevated temperature, flow through the micrometer sized pores is unimpeded.

"Smart" polymers responsive to changes in pH, temperature, and irradiation have been reported in the literature to have been used in applications such as drug delivery, encapsulated enzyme bio-reactors, and the formation of membranes with controlled permeability. The state-of-the-art in this area has been reviewed recently by Galaev (Russian Chemical Reviews 64, 471–489, 1995).

Galaev discloses using the ability of "smart" polymers to undergo transformation from an uncoiled globule into a compact coil to create membranes with controllable permeability (at 478), it produces structures which exhibit exactly the opposite behavior than exists in the present invention. In Galaev's compact conformation, the "smart" polymer molecules block or strongly hinder the entry of a solute into the pores of the membrane. In the present invention, when the thermally responsive polymer is in its compact form (at high temperature), flow through the monolith is unimpeded.

Galaev also makes reference to a system wherein purification of an enzyme is performed by elution solely as a result of changing the temperature without any alteration of the composition of the buffer (at 482). The system described, however, contains but a single enzyme in a solution and removes that enzyme by adsorption to a "smart" polymer attached to packed beads. The system can not separate two or more enzymes from each other as can the present invention.

U.S. Pat. No. 5,426,154 discloses thermally reversible graft copolymers comprising a vinyl polymer graft copolymerized to a polymer of N-substituted acrylamide or methacrylamide derivatives.

Hydrogel membranes with temperature-controlled permeability for molecules of different sizes (Fief et al., Journal of Membrane Science, 1991, 64, 283) and polarity (T. Ogata et al, Journal of Membrane Science, 1995, 103, 159) were prepared directly by the copolymerization of N-isopropylacrylamide (NIPAAm) with a comonomer and a crosslinking agent. A decrease in the permeability of these membranes was observed at temperatures exceeding the lower critical solution temperature (LCST). This is the opposite of the behavior which occurs in the monoliths of this invention.

NIPAAm has also been grafted onto the surface of commercial polyamide membranes using W irradiation initiated polymerization and the resulting membrane showed a temperature dependent permeation of riboflavin. (Lee et al, Polymer, 1995, 36, 81)

Thin porous glass membranes were modified with vinyldimethylchlorosilane and then polymerization of N-isopropylacrylamide was effected by a redox system to produce composite membranes whose permeability increased above the LCST (Konno et al. in Polymer Gels [Ed. D. DeRossi], Plenum Press, New York, 1991, 173).

Similarly, the volume transition exhibited by NIPAAm in response to changes in temperature was used to control the pore size of beads grafted with NIPAAm in gel permeation chromatography and packed in chromatographic columns. For example, Gewehr et al. (*Makromolekulare. Chemie,* 1992, 193, 249) reacted carboxyl terminated PNIPAAm with amino groups functionalized porous glass beads and observed differences in exclusion limits of the composite upon changes in temperature. Hosoya et al. (Macromolecules, 1994, 27, 3973) used the process of U.S. Pat. No. 5,306,561 to produce polymer beads with a thermoresponsible surface layer that controls the access of compounds to the interior of the beads. However, since flow in a column packed with particles/beads occurs through the interstitial voids between packed particles, these grafted beads are not capable of forming thermal valves or thermal gates as in the present invention.

U.S. Pat. Nos. 5,334,310 and 5,453,185 disclose a process for preparing a continuous liquid chromatography column and a column containing a new class of macroporous polymer materials prepared by a simple molding process. The porous polymer monoliths are characterized by a unique bimodal pore distribution, consisting of large generally micrometer-sized convective pores and much smaller diffusive pores. High flow rates through the monoliths are obtained at low back pressures due to the network of the large canal-like convective pores which traverse the length of the monolith. It has now been discovered that unique flow-through properties can be imparted to these and other porous polymer materials by grafting the pores with thermally responsive polymer chains.

The concept of hydrophobic interaction chromatography (HIC) is based on the interaction of hydrophobic patches located on proteins with hydrophobic ligands located on a separation medium in an environment, such as an aqueous salt solution, that promotes these interactions. The column-bound ligands are typically short alkyl chains or phenyl groups. The strength of the interaction depends on many factors such as the intrinsic hydrophobicity of the protein, the type of ligands, their density, the separation temperature, and the salt concentration. Typically, the separation of two or more proteins is achieved by decreasing the salt concentration in the mobile phase, causing the less hydrophobic molecules to elute first. In contrast to highly hydrophobic reversed-phase chromatographic media that require elusion with organic solvents, the column surface incorporates a much lower density of ligands interspersed within a highly hydrophilic surface, allowing elusion with entirely aqueous eluents. The original column packings for hydrophobic interaction chromatography were derivatives of polysaccharide gels. Currently, a wide variety of hydrophobic media based on both inorganic and organic polymer beads is available for HIC. However, the re-equilibration of the column in the initial mobile phase after each analysis is a serious limitation for high throughput processes.

In prior isocratic hydrophobic interaction chromatography, a gradient solvent system with an increasing ionic strength was used to perform the elusions. In the present invention, however, a single solvent system at a single ionic strength, but at varying temperature, is used to perform the separation of two or more biomolecules, e.g. proteins, from each other.

Accordingly, it is an object of the present invention to provide thermally responsive polymer monoliths, particularly porous monoliths which are capable of functioning as thermal gates or thermal valves, more particularly porous monoliths suitable as a hydrophobic interaction chromatography substrate.

It is a further object to modify the internal pore surface of a polymer monolith with thermally responsive polymer chains.

It is a still further object to produce a polymer structure suitable for use in isocratic hydrophobic interaction chromatography wherein a single solvent is used to elute different proteins depending upon temperature.

These and still further objects will be apparent from the ensuing detailed disclosure of this invention.

SUMMARY OF THE INVENTION

This invention is directed to a porous polymer monolith wherein flow through the body is controlled by varying the temperature of the body. More particularly, the invention is directed to a porous polymer monolith wherein a thermally responsive polymer is grafted to the pores of the polymer monolith by a two-step grafting procedure which generally entails (i) vinylization of the pores followed by (ii) in situ free radical polymerization of a vinyl monomer or mixture of vinyl monomers which will graft the thermally sensitive polymer to the pores.

This invention is further directed to a polymer monolith having pores wherein the surfaces of the pores have thermally responsive polymer chains attached thereto.

This invention is further directed to a polymer monolith which precludes or reduces flow through the monolith at a first temperature and which permits maximum flow through the monolith at a second, higher temperature.

This invention is further directed to a method of performing isocratic hydrophobic interaction chromatography to separate a mixture of biomolecules by the use of a mobile phase with a constant salt concentration. The method entails injecting a mixture of bio-molecules into a porous polymer monolith of a first polymer having grafted thereon a second polymer which is thermally responsive, the injecting being at a first temperature which is above the lower critical solution temperature of the thermally responsive polymer; eluting a first bio-molecule among the mixture of biomolecules with the mobile phase at the first temperature; decreasing the temperature to a second temperature below the lower critical solution temperature; and eluting a second biomolecule from among the mixture of biomolecules with the mobile phase.

DETAILED DESCRIPTION OF THE INVENTION

Figure 1:
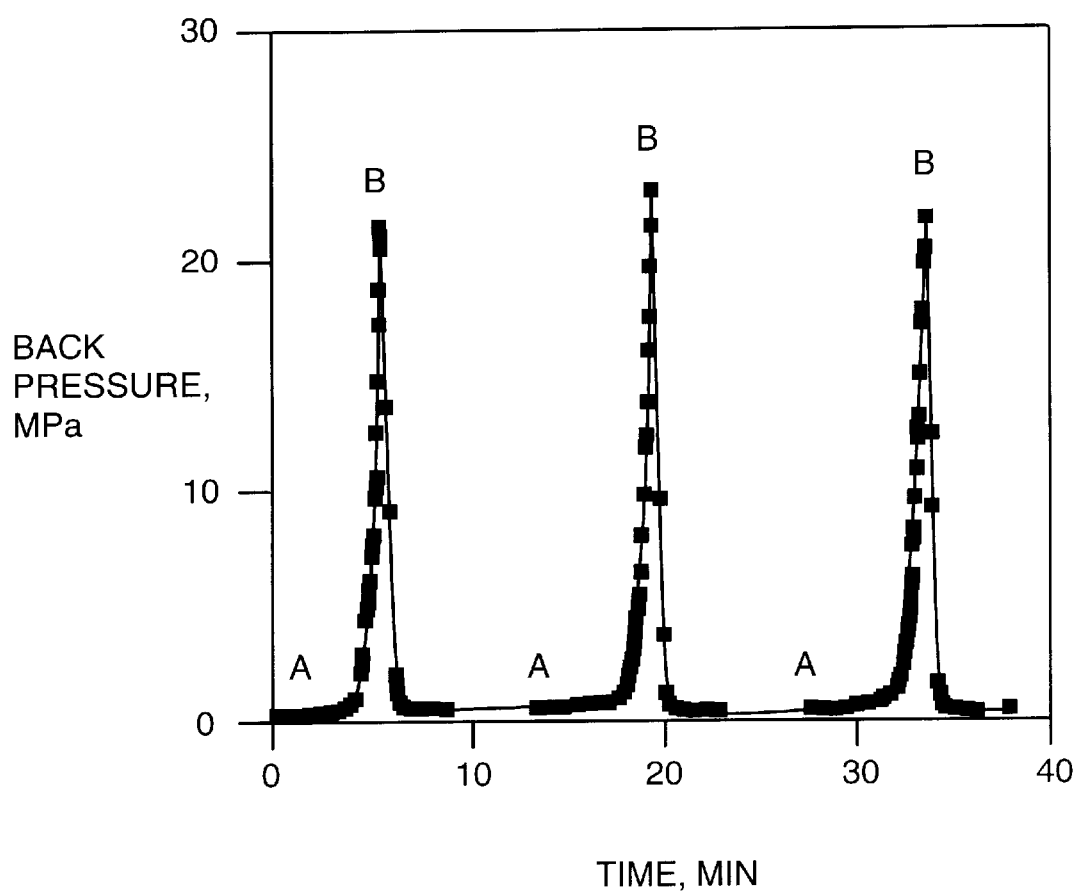
FIG. 1 is a graph of back pressure vs. time showing thermal gate flow properties of a porous poly(glycidyl methacrylate-co-ethylene dimethacrylate) monolith grafted with poly(N-isopropylacrylamide) in accordance with this invention. Points A indicate removal of the monolith from a 40° C. bath and points B indicate reimmersion of the monolith into the 40° C. bath.

A polymer monolith is a solid polymer body containing a sufficient amount of pores greater than about 600 nm in diameter that a liquid can pass through the body under conditions of convective flow. The monolith is distinguished from a packed bed of polymer beads in which convective flow through the bed occurs predominately, if not exclusively, through the interstices between beads and not through any single bead. The monolith has a thickness of about 5 mm or more, as contrasted with thin membranes which have thicknesses on the order of several microns. Preferably, the monolith is an elongated generally rod-shaped body having a thickness (or length) of from about 5 to about 100 mm.

Preferred monoliths are the plugs disclosed in U.S. Pat. Nos. 5,334,310 and 5,453,185, the subject matters of which are incorporated herein by reference. These preferred polymer monoliths are characterized by possessing a bimodal pore distribution, containing both large generally micrometer-sized convective pores and much smaller diffusive pores. As a result of the large canal-like convective pores which traverse the length of these monoliths, a high flow rate through the monoliths may be obtained at low back pressure.

The preferred polymer monolith is prepared by polymerizing a polyvinyl monomer or, more preferably, a mixture of a polyvinyl monomer and a monovinyl monomer, in the presence of an initiator and a porogen. The polymerization mixture may also contain macroporous polymeric particles. The polymerization mixture is added to a column and polymerization is initiated therein so as to form the polymer monolith, i.e. plug. The polymer monolith is then washed with a suitable liquid to remove the porogen.

Suitable polyvinyl monomers useful for preparing the monolith include divinylbenzene, divinylnaphthalene, divinylpyridine, alkylene dimethacrylates, hydroxyalkylene dimethacrylates, hydroxyalkylene diacrylates, oligoethylene glycol dimethacrylates, oligoethylene glycol diacrylates, vinyl esters of polycarboxylic acids, divinyl ether, pentaerythritol di-, tri-, or tetramethacrylate or acrylate, trimethylopropane trimethacrylate or acrylate, alkylene bisacrylamides or methacrylamides, and mixtures of any such suitable polyvinyl monomers. The alkylene groups generally contain about 1–6 carbon atoms.

Monovinyl monomers which may be used to prepare the monoliths include styrene, ring substituted styrenes wherein the substituents include chloromethyl, alkyl with up to 18 carbon atoms, hydroxyl, t-butyloxycarbonyl, halogen, nitro, amino group, protected hydroxyls or amino groups, vinylnaphthalene, acrylates, methacrylates, vinylacetate, vinylpyrrolidone, and mixtures thereof. The polyvinyl monomer or polyvinyl monomer plus the monovinyl monomer are generally present in the polymerization mixture iii an amount of from about 10 to 60 vol %, and more preferably in an amount of from about 20 to 40 vol %.

The porogen used to prepare the monolith may be selected from a variety of different types of materials. For example, suitable liquid porogens include aliphatic hydrocarbons, aromatic hydrocarbons, esters, alcohols, ketones, ethers, solutions of soluble polymers, and mixtures thereof. The porogen is generally present in the polymerization mixture in an amount of from about 40 to 90 vol %, more preferably from about 60 to 80 vol %.

Monomers useful to form the thermally responsive polymers which are grafted onto the surface of the pores within the monolith are known. Suitable such monomers include acrylamides and methacrylamides substituted on the nitrogen atom with one or two $C_2$–$C_5$ alkyl, cyclopropyl, $C_2$–$C_4$ alkylaminoalkyl or dialkylaminoalkyl, $C_1$–$C_4$ methoxyaminoalkyl, $C_1$–$C_4$ dimethoxy or diethoxyamincalkyl, $C_1$–$C_4$ methoxyalkyl, tetrahydopyranyl, and tetrahydrofurfuryl groups, N-acryloylpiperidine and N-acryloylpyrrolidone, vinylcaprolactam, methyl vinyl ether, 3-hydroxypropylacrylate, vinyl acetate, 2-($C_2$–$C_6$)-alkyl-l-vinyloxazolines, ethylene oxide, propylene oxide, as well as copolymers thereof with copolymerizable comonomers which do not preclude thermal responsiveness of the resulting polymer. Suitable comonomers, e.g. methylenebisacrylamide with N-alkylacrylamide, may be used to provide crosslinking and controllable swelling or other desirable properties. Preferred monomers are N-alkyl ($C_3$–$C_6$) acrylamides, N-alkyl ($C_3$–$C_6$) methacrylamides, and vinyl alkyl ($C_1$–$C_4$) ethers. Polymers produced from these monomers undergo a rapid and reversible phase transition from a first structure, generally extended, below their lower critical solution temperature (LCST) to a second, generally collapsed, structure above the LCST. Thus, they are sometimes referred to as "thermo-shrinking" polymers. Poly(N-isopropylacrylamide) (PNIPAAm) is perhaps the best known of the class of temperature sensitive polymers and undergoes the phase transition at 32° C.

In contrast to the stepwise transition behavior typical of linear and slightly crosslinked homopolymers of the above monomers characterized by a single sharp LCST, copolymers of these monomers with monomers such as $C_1$–$C_8$ alkyl acrylates and methacrylates, styrene and its substituted derivatives, and acrylonitrile, can provide a slower change in their properties over a longer range of temperatures.

It is preferred to attach a thermally responsive polymer to the surfaces within the polymer monolith using surfaces that contain an adequate number of polymerizable double bonds. Generally, the pore surfaces must be functionalized by placing reactive vinyl groups thereon. Then the vinyl monomers which form the thermally responsive polymer can be polymerized in situ within the monolith. Any unreacted double bonds of the crosslinking monomer used to prepare the monolith which are on a surface of the monolith will enter into the polymerization reaction. If the amount of unreacted double bonds is sufficiently high, there may be little or no need to functionalize the pore surfaces prior to polymerization of the thermally responsive polymer. A thermally responsive polymer thereby is simultaneously formed within the pores of the monolith and chemically grafted thereto. Suitable compounds for attaching vinyl groups to the internal surfaces of the preferred monoliths described above are allylic compounds which contain a chemical group reactive with the surface of the polymer monolith. Examples of such compounds include allylamine, allylbromide, maleic anhydride, methacroyl and acryloylhalide, methacroyl and acryloylanhydride.

An example of the two-step grafting process is summarized in Scheme 1 for a polymer monolith prepared from poly(glycidyl methacrylate-co-ethylene dimethacrylate) (GMA-EDMA) (1). Pendant epoxide groups on its surface are reacted with allyl amine (2). Then, an in situ free radical polymerization of N-isopropylacrylamide (NIPAAm), optionally with methylenebisacrylamide (MBAAm) crosslinking agent to control the swelling, is performed to produce the thermally responsive monolith (3). While the catalyst indicated is 2,2'-azobisisobutyronitrile (AIBN), any free radical generating catalyst or catalyst system may be used, including such as other azo catalysts, peroxides, redox couples, and the like.

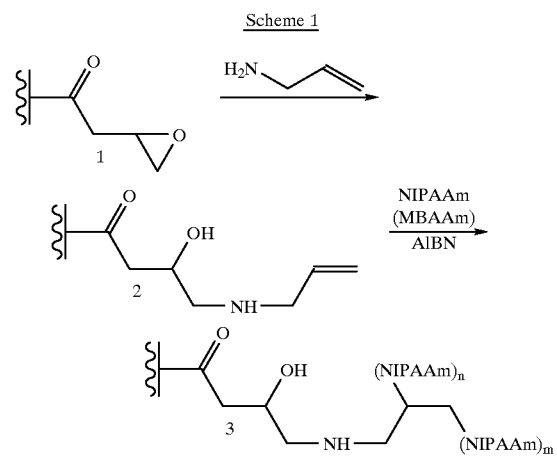

Scheme 1

The monolith (3) thus produced changes its properties in response to changes in external temperature. When no crosslinking agent monomers are present during the in situ polymerization, the monolith performs as a thermal gate that provides thermal "on/off" behavior to fully open the micrometer sized pores at a temperature above the LCST and to fully close the pores at a temperature below the LCST. When crosslinking monomers are present during the in situ polymerization, the monolith performs as a thermal valve, expanding or contracting within the pore but not fully blocking the pore, to provide control of the flow rate through the monolith.

The thermal switching behavior has been found to also effect surface polarity. Thus there is a thermally controlled change of the surface from hydrophobic to hydrophilic. The extended chains that prevail below the LCST are more hydrophilic, while the collapsed chains that exist above the LCST are more hydrophobic. This change in surface polarity makes the thermally responsive polymer monolith especially suitable for use as a support in isocratic hydrophobic interaction chromatography.

Further information about the present invention is provided in the following illustrative examples in which all parts and percents are by weight unless otherwise specified.

EXAMPLE 1

Preparation of Thermal Gate

Preparation of Polymer Monolith

All materials were used as received, except for the N-isopropyl acrylamide (NIPAAm), which was recrystallized from hexane and dried at room temperature in vacuo. All monoliths were prepared in 10×10 mm i.d. stainless steel cartridges using a reaction mixture containing 24 vol % glycidyl methacrylate (GMA), 16 vol % ethylene dimethacrylate (EDMA) and 60 vol % cyclohexanol (porogenic solvent). 2,2'-Azobisisobutyronitrile (AIBN, 1 wt % with respect to monomers) was dissolved in the mixture, and the mixture was purged with nitrogen for 10 minutes. The columns were filled with the mixture, and the polymerization was allowed to proceed for 20 hours at a temperature of 55° C. Upon completion, the columns were fitted with threaded end pieces containing 2 µm frits and placed inside a corresponding stainless steel holder. The holder was attached to an HPLC system, and 25 mL tetrahydrofuran was pumped through the column to remove the porogenic solvent and any soluble compounds that remained in the monoliths at the end of the polymerization.

Reaction with Allyl Amine

The polymer monolith was washed with 25 mL of water and 5 mL of a 50 wt % aqueous solution of allyl amine was then flushed through the column at 1 mL/min using a syringe pump (Sage Instruments, Model 341A). The imbibed column was sealed and placed in a 60° C. bath for 8 hours. After the reaction was completed, water was pumped through the column to remove any excess amine. This was continued until the pH of the effluent returned to the value for distilled water.

Grafting Polymerization Reaction to Prepare Thermal Gate

The grafting solution used for the preparation of the thermal gate consisted of 10 wt % NIPAAm in benzene. A free radical initiator (AIBN) (1 wt % with respect to monomer) was dissolved in the mixture and the mixture was purged with nitrogen for 10 minutes. The allyl amine mod) fied column was washed with 5 mL tetrahydrofuran and 10 mL of benzene. 5 mL of the grafting solution was pumped through the column, the column sealed, and placed in a 60° C. bath for 20 hours. After the reaction was completed, the column was washed with 40° C. warm water.

Analysis

Confirmation of the presence of grafted PNIPAAm was provided by (i) an appearance of amide I (1647 cm$^{-1}$) and amide II (1456 cm$^{-1}$) bands in FT-IR spectra recorded from KBr disks; (ii) an increase of 0.6–0.8 wt % in nitrogen content, as determined by elemental analysis, compared to that found for the original allyl amine functionalized monoliths, which corresponds to values of 4.8–6.5 wt % of PNIPAAm grafted to the monolith; (iii) an endotherm at 31.5 C in the DSC curve of the polymer equilibrated in water overnight; and (iv) the behavior as shown in Example 2 below.

EXAMPLE 2

To evaluate the performance characteristic of the modified monolith of Example 1, a Waters HPLC system consisting of two 510 HPLC pumps and a 486 W detector was used to carry out back pressure measurements. The data was acquired and processed with Millennium 2010 software (Waters).

The monolith modified with PNIPAAm was equilibrated with water pumped at a flow rate of 1 mL/min through the column immersed in a bath heated to 40° C. At this temperature, the chains existed in their collapsed or compact form, and there was little resistance to flow. The column was then removed from the bath (points A of FIG. 1) while the flow of water was allowed to continue. Within a very short period of time, the temperature reduced to room temperature (about 25° C.) and the back pressure quickly increased as the grafted PNIPAAm chains expanded and filled the pores completely. When the back pressure approached the operational limit of the pump, the column was reimmersed in the 40° C. bath (points B of FIG. 1) and the back pressure returned almost immediately to its original value. FIG. 1, a graph of back pressure vs. time of this Example, clearly documents that the gate effect is rapid, reversible and reproducible.

COMPARATIVE EXAMPLE A

To demonstrate that the PNIPAAm chains were indeed grafted to the monolith pore surface, the grafting procedure of Example 1 was repeated with a macroporous monolith of the same composition which had not previously been vinylized with allyl amine. Rather, it was subjected only to the same in situ polymerization with NIPAAm.

While a few polymer chains were likely grafted to some unreacted double bonds of the ethylene dimethacrylate (EDMA) used to prepare the monolith, when the resulting monolith was evaluated as in Example 2, it exhibited no temperature dependent behavior, i.e. the number of reactive unreacted double bonds was too low to allow any substantial polymer grafting to occur such that temperature dependent behavior existed.

EXAMPLE 3

The procedure of Example 1 was repeated except that the grafting solution contained 9.9 wt % NIPAAm and 0.1 wt % methylenebisacrylamide (MBAAm) in benzene. According to the Poiseuille-Hagen law a decrease in a tube diameter leads to a decrease in the flow rate of a liquid through the tube at constant pressure drop, or requires a higher applied pressure to achieve the same flow rate. Therefore, back pressure measurements at a constant flow rate can be used to determine changes in the diameter of a tube. Although the monolith was permeated with pores having very different shapes from those of a regular tube, increases in the back pressure can be directly measured and used for monitoring changes in the pore size.

Figure 2:
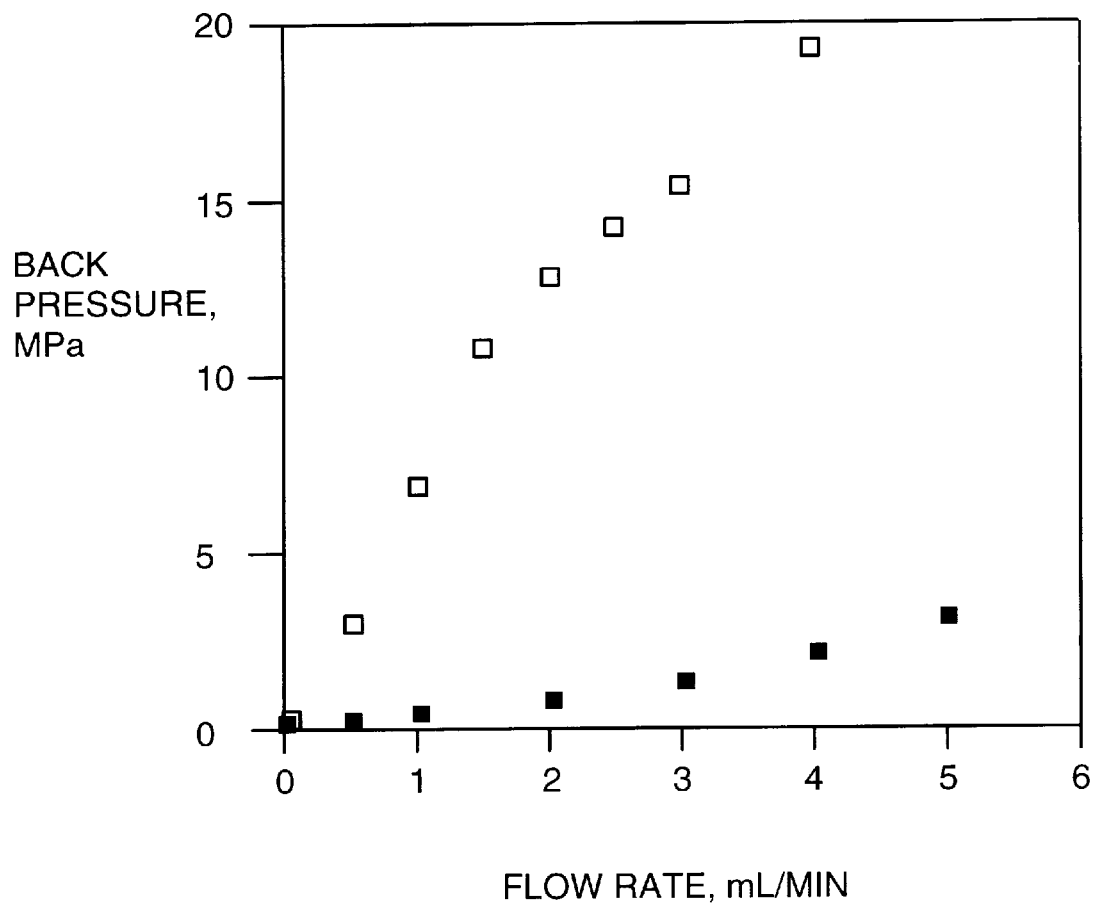
FIG. 2 is a graph of back pressure vs. flow rate showing thermal valve flow properties of a porous poly(glycidyl methacrylate-co-ethylene dimethacrylate) monolith grafted with poly(N-isopropyl acrylamide-co-methylenabisacrylamide) in accordance with this invention. The back pressure of water at temperature 25° C. is shown with □ and at temperature 40° C. with ■.

Accordingly, the flow rate of water through the resulting monolith was evaluated as a function of temperature using the equipment of Example 2. FIG. 2 shows the effect of temperature on the back pressure profile for a 10 mm thick monolithic block modified with a grafting solution which contained MBAAm in addition to NIPAAm. Unlike the thermal gate behavior exhibited by the monolith of Examples 1 and 2, flow proceeded through the monolith regardless of whether the grafted chains existed in their extended or collapsed forms. Rather, it was the rate of the flow which varied depending upon the temperature. This behavior is referred to herein as a "thermal valve". This thermal valve behavior resulted from the fact that the MBAAm crosslinking did not allow the chains to swell to an extent sufficient to fill the pores completely. The back pressure at different flow rates was always much higher at a temperature of 25° C.(□) than at 40° C.(■). Thus, grafting in the presence of a crosslinker leads to a composite material in which thermal control of flow rate can be effected.

EXAMPLE 4

Isocratic Hydrophobic Interaction Chromatography

In light of the excellent mass transport properties of the polymeric monolith and their particularly effective application in the separation of macromolecules, the thermally induced change in surface polarity of the grafted composites was also tested to achieve an isocratic chromatographic separation of proteins in the hydrophobic interaction mode.

Figure 3:
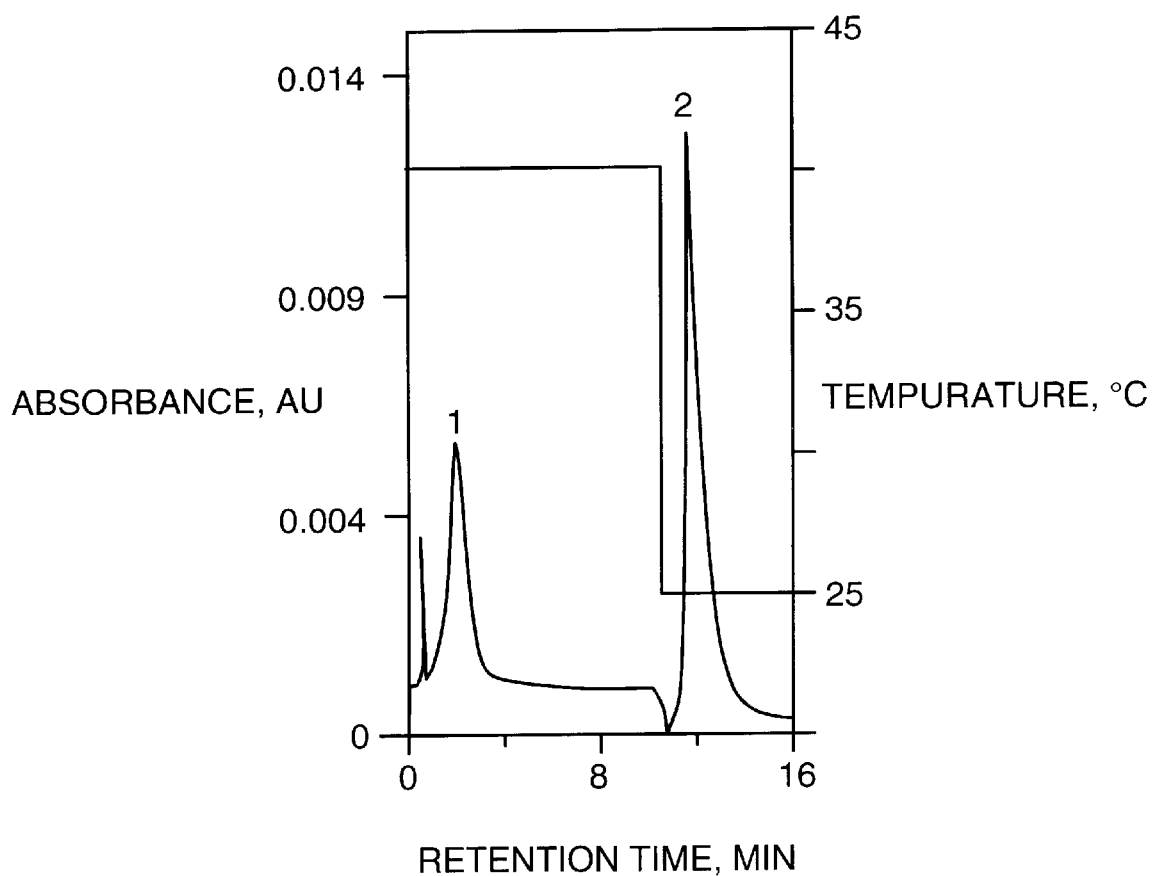
FIG. 3 shows the temperature controlled separation of carbonic anhydrase (1) and soybean trypsin inhibitor (2) using a porous poly(glycidyl methacrylate-co-ethylene dimethacrylate) monolith grafted with poly (N-isopropylacrylamide-co-methylene bisacrylamide) using hydrophobic interaction chromatography in accordance with this invention. The mobile phase was 1.4 mol/L ammonium sulfate in 0.01 mol/L phosphate buffer (pH 7) at a flow rate of 1 mL/min.

The monolith of Example 3 was used to separate proteins at a constant salt concentration by utilizing the hydrophobic-hydrophilic transition of the grafted chains in response to a change in temperature. FIG. 3 shows the isocratic separation of carbonic anhydrase and soybean trypsin inhibitor. First, a 10 mm thick monolithic rod was modified as in Example 3 with a grafting solution containing NIPAAm and MBAAm was heated to 40° C. Then a mixture of the two proteins was injected through a Rheodyne 7725 valve loop injector into the column in a 1.4 mol/L ammonium sulfate solution at a flow rate of 1 mL/min and monitored at 280 nm.

The more hydrophilic carbonic anhydrase was not retained under these conditions and eluted immediately from the column. In contrast, the more hydrophobic trypsin inhibitor did not elute even after ten minutes. However, once the temperature of the column was lowered to 25° C., the more hydrophobic trypsin inhibitor protein eluted almost immediately.

COMPARATIVE EXAMPLE B

To demonstrate that the PNIPAAm chains grafted to the monolith pore surface are responsible for the isocratic hydrophobic chromatographic separation, a macroporous monolith of Comparative Example A which had not been vinylized with allyl amine and was subjected only to the same in situ polymerization with NIPAAm, was used in a separation. Evaluation as in Example 4 did not lead to any separation.

What is claimed is:

1. A composite polymer monolith wherein a thermally responsive polymer is grafted to the surface of pores within a rigid porous polymer monolith by a two-step grafting procedure comprising the steps of (i) vinylization of the pores followed by (ii) in situ polymerization of a monomer which forms a thermally responsive polymer within said pores.

2. The monolith of claim 1, wherein the monolith has an elongated body with a thickness of from about 5 to about 100 mm.

3. The monolith of claim 1, wherein the monolith has a bimodal pore distribution.

4. The monolith of claim 1, wherein at one temperature the thermally responsive polymer blocks flow through the monolith and at a second temperature allows flow through the monolith.

5. A polymer monolith having pores through which a liquid may pass, said pores containing a grafted thermally responsive polymer, wherein flow of the liquid through the monolith does not occur at a first temperature and does occur at a second higher temperature.

6. The monolith of claim 5, wherein the monolith has an elongated body having a thickness of from about 5 to about 100 mm.

7. The monolith of claim 5, wherein the monolith has a bimodal pore distribution.

8. The polymer monolith of claim 5 wherein the first temperature is about 25° C.

9. The polymer monolith of claim 5 wherein the second temperature is about 40° C.

10. The polymer monolith of claim 5 wherein the thermally responsive polymer is a polymer selected from the group consisting of polymers of acrylamides and methacrylamides substituted with one or two $C_2$–$C_5$ alkyl, cyclopropyl, $C_2$–$C_4$ alkylaminoalkyl or dialkylaminoalkyl, $C_1$–$C_4$ methoxyaminoalkyl, $C_1$–$C_4$ dimethoxy or diethoxyaminoalkyl, $C_1$–$C_4$ methoxyalkyl, tetrahydopyranyl, and tetrahydrofurfuryl groups on the nitrogen atom; N-acryloylpiperidine and N-acryloylpyrrolidone; vinylcaprolactam; methyl vinyl ether; 3-hydroxypropylacrylate; vinyl acetate; 2-($C_2$–$C_6$)-alkyl-1-vinyloxazolines; ethylene oxide; and propylene oxide.

11. The polymer monolith of claim 5 wherein the thermally responsive polymer is poly(N-isopropylacrylamide).

12. The polymer monolith of claim 5 wherein the thermally responsive polymer is more hydrophilic below the first temperature as compared to the same polymer at the second higher temperature.

13. A polymer monolith having internal pores through which a liquid may pass, said pores containing a grafted thermally responsive polymer, wherein the rate of flow of the liquid through the monolith is controlled by the temperature of the monolith.

14. The monolith of claim 13, wherein the monolith has an elongated body with a thickness of from about 5 to about 100 mm.

15. The monolith of claim 13, wherein the monolith has a bimodal pore distribution.

16. The polymer monolith of claim 13, wherein the thermally responsive polymer comprises a copolymer having repeating monomer units selected from the group consisting of acrylamides and methacrylamides, substituted on the nitrogen atom, with one or two $C_2$–$C_5$ alkyl, cyclopropyl, $C_2$–$C_4$ alkylaminoalkyl or dialkylaminoalkyl, $C_1$–$C_4$ methoxyaminoalkyl, $C_1$–$C_4$ dimethoxy or diethoxyamincalkyl, $C_1$–$C_4$ methoxyalkyl, tetrahydopyranyl, tetrahydrofurfuryl groups, N-acryloylpiperidine and N-acryloylpyrrolidone, vinylcaprolactam, methyl vinyl ether, 3-hydroxypropylacrylate, vinyl acetate, 2-($C_2$–$C_6$) -alkyl-1-vinyloxazolines, ethylene oxide, propylene oxide, $C_1$–$C_8$ alkyl acrylates and methacrylates, styrene, substituted derivatives of styrene, and acrylonitrile.

17. The polymer monolith of claim 13 wherein the thermally responsive polymer is a copolymer of N-isopropylacrylamide and a copolymerizable monomer.

18. An method for obtaining an isocratic hydrophobic interaction chromatographic separation of biomolecules using a mobile phase with a constant salt concentration which comprises the steps of:

(i) injecting a mixture of bio-molecules into a porous polymer monolith of a first polymer having grafted thereon a second polymer which is thermally responsive, the injecting being at a first temperature which is above the lower critical solution temperature of the thermally responsive polymer;

(ii) eluting a first bio-molecule among the mixture of biomolecules with the mobile phase at the first temperature;

(iii) decreasing the temperature to a second temperature below the lower critical solution temperature; and (iv) eluting a second biomolecule from among the mixture of biomolecules with the mobile phase.

19. The separation of biomolecules of claim 18, wherein the first bio-molecule comprises a first protein and the second biomolecule comprises a second protein, the first protein being more hydrophilic than the second protein.

* * * * *